United States Patent [19]
Munk et al.

[11] Patent Number: 6,087,361
[45] Date of Patent: *Jul. 11, 2000

[54] ARYL-IMIDAZOLINES AND ARYL-IMIDAZOLES USEFUL AS α-2 ADRENERGIC AGONISTS WITHOUT CARDIOVASCULAR SIDE EFFECTS

[75] Inventors: Stephen A. Munk, Northville, Mich.; James A. Burke, Tustin; Ronald K. Lai, Irvine, both of Calif.

[73] Assignee: Allergan Sales, Inc., Irvine, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/971,952

[22] Filed: Nov. 17, 1997

Related U.S. Application Data

[63] Continuation-in-part of application No. 08/647,130, May 9, 1996, abandoned, which is a continuation-in-part of application No. 08/440,030, May 12, 1995, abandoned.

[51] Int. Cl.[7] .................................................... A61K 31/56
[52] U.S. Cl. .......................................... 514/249; 514/397
[58] Field of Search ...................... 514/397, 249

[56] References Cited

U.S. PATENT DOCUMENTS

| | | | |
|---|---|---|---|
| 3,459,763 | 8/1969 | Gruenfeld . | |
| 5,077,292 | 12/1991 | Gluchowski | 514/249 |
| 5,091,528 | 2/1992 | Gluchowski . | |
| 5,112,822 | 5/1992 | Gluchowski . | |
| 5,663,189 | 9/1997 | Maurer et al. | 514/397 |

FOREIGN PATENT DOCUMENTS

95/01150  1/1995  WIPO .

OTHER PUBLICATIONS

Ernsberger et al, "A Second Generation of Centrally Acting Antihypertensive Agents Act on Putative $I_1$–Imidazoline Receptors", Journal of Cardiovascular Pharmacology 20 (Suppl. 4), S1–S10 1992.

U. S. Application No. 08/086,482, Maurer et al., filed on Jul. 1, 1993.

Bousquet et al, "Imidazoline Receptors A New Concept in Central Regulation of the Arterial Blood Pressure", American Journal of Hypertension, Inc., 1992:5:47S–50S.

Physical Organic Chemistry, N.S. Isaacs Universities Press (Belfast) Ltd., 1987 pp. 62–67.

Wilson and Gisvold's Textbook of Organic Medicinal and Pharmaceutical Chemistry, R.F. Doerge (ed.) J.B. Lipincott Co. 1982, pp. 41–43.

Jen et al, "Amines and Related Compounds. 6[1] Studies on Structure–Activity Relationships of Antihypertensive and Antisecretory Agents Related to Clonidine", J. Med. Chem., 18(1), 90–99(1975).

Ruffolo RR, Jr. (ed): α–Adrenoceptors: Molecular Biology, Biochemistry and Pharmacology, Prog. Basic Clin Pharmacol, Basel, Karger, 1991, vol. 8, pp. 75–114.

M.C. Michel and P. Ernsberger in TiPS, 13, pp. 369–379 (Oct. 1992).

Haxhiu, M.A., et al, J. Cardiovasc. Pharmacol. 24(suppl. 1) pp. S1–S8 (1994).

Harron, D.W. [Am. J. Hypertens., 5(4,Pt.2) pp. 91S–98S9Apr. 1992).

Codd, E.E., et al. Life Sci., 56(2) p. 63–74(Dec. 2, 1994).

Ernsberger, P., et al, Cardivasc. Drugs Ther., 8(Suppl. 1) pp. 27–41(Mar. 1994).

Jin, Y. et al, J. Ocul. Pharmacol., 10(1) pp. 359–369(1994).

Millan, M., J. Eur. J. Pharmacol., 215(2–3)pp. 355–356(1992).

CA 114:63020, Anderman, 1990.

CA 95:12796, Newsome et al, 1981.

CA 118:66873, Sims et al, 1992.

Primary Examiner—Keith D. MacMillan

[57] ABSTRACT

Methods are disclosed for treating a mammal with a condition that responds to α2 agonist treatment without causing cardiovascular side effects using compounds of the formula

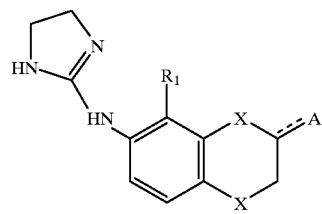

wherein $R_1$ is H, alkyl or 1 to 4 carbon atoms or a halogen atom, X is O or NH and A is H or an oxo group and wherein said compound does not cause a concomitant reduction in blood pressure of said mammal.

7 Claims, 2 Drawing Sheets

ARYL-IMIDAZOLINES AND ARYL-IMIDAZOLES USEFUL AS α-2 ADRENERGIC AGONISTS WITHOUT CARDIOVASCULAR SIDE EFFECTS

This application is a continuation-in-part of Ser. No. 08/647,130 filed May 9, 1996, abnd., which is a continuation-in-part of Ser. No. 08/440,030 filed May 12, 1995, abnd.

FIELD OF THE INVENTION

The present invention relates to meta-substituted aryl linked imidazolines and imidazoles. More particularly, the invention relates to such compounds which have $\alpha_2$ adrenergic agonist activity.

BACKGROUND OF THE INVENTION

Aryl-2-amino-imidazolines are well-known in the art. Compounds such as moxonidine, para-aminoclonidine, brimonidine and tramazoline are but a few of the compounds which contain this basic structural feature that have also found use as therapeutic agents. For a review of structure activity relationships of this type of compound in relation to adrenergic receptors see R. Ruffolo, Jr. (ed.) in α-Adrenoreceptors: Molecular Biology, Biochemistry and Pharmacology, Prog. Basic Clin. Pharmacol. (Basel, Karger), 8 pp. 75–114 (1991).

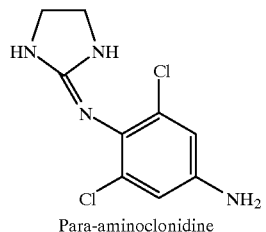
Para-aminoclonidine

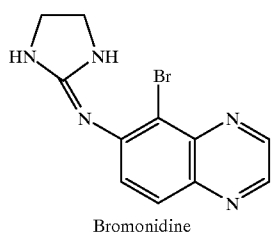
Bromonidine

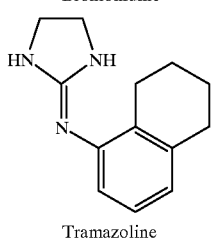
Tramazoline

A compound of similar structure is moxonidine. However, moxonidine has been identified pharmacologically as a selective imidazoline receptor agonist, with utility as a centrally-acting antihypertensive agent. The pharmacological investigation of imidazoline agents independent of adrenoceptors started in the mid-1980's. Two major subtypes, tentatively designated $I_1$ and $I_2$, are recognized. $I_1$ sites are labeled with nanomolar affinity by clonidine analogs whereas $I_2$ sites have micromolar affinity for clonidine and are usually labeled by tritiated idazoxan. The 'I' designation (for imidazoline) has been intended to encompass not only imidazolines, imidazoles, and imidazolidines, but also such related structures as guanidines and oxazolines, all of which are potential ligands at these sites. A recent review of imidazoline-preferring receptors has been published by M. C. Michel and P. Ernsberger in TiPS, 13, pp. 369–379 (Oct. 1992).

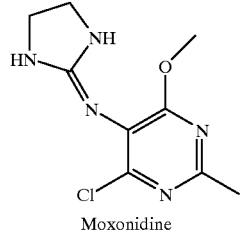
Moxonidine

Studies to identify the mechanism of the selective antihypertensive action of moxonidine have shown that the effect is mediated mainly by $1_1$-imidazoline receptors in the rostral ventrolateral medulla. [Haxhiu, M. A. et al, J. Cardiovasc. Pharmacol. 24 (suppl.1) pp. S1–S8 (1994)]. Similar studies of related compounds have identified rilmenidine as a hypotensive drug that is more selective for imidazoline receptors than for classical $\alpha_2$ adrenoceptors [Bousquet, P., et al., Am. J. Hypertens. 5 pp 47S–50S, 1992]. The rilmenidine structure substitutes an oxazolidine ring for imidazoline. Such heterocyclic ring substitutions are noted in the Ruffolo monograph on page 99 to reduce or abolish activity at $\alpha_2$ receptors. A study published by Harron, D. W. (Am. J. Hypertens., 5(4, Pt. 2) pp. 91S–98S (April 1992) reported that in experimental studies, "rilmenidine differs from clonidine in that it is more selective for imidazoline receptors than for $\alpha_2$-adrenoceptors; at equihypotensive doses, rilmenidine causes less bradycardia and reduction in cardiac output, less sedation, and little or no antinociceptive action compared to clonidine".

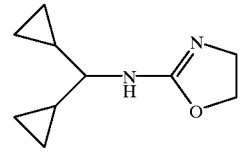
Rilmendine

A few aryl-2-amino-imidazole derivatives are known in the pharmaceutical arts: Jen, et al in *J. Med. Chem.*, 18(1). 90–99 (1975) made and tested a clonidine analog, among a few other related structures for antihypertensive and gastric antisecretory activity. U.S. Pat. No. 3,459,763 (to Gruenfeld) which discloses a variety of substituted imidazole compounds, the two classes of compounds disclosed are regioisomers of the general structures: phenyl-2-amino-imidazole and N-1-phenyl-2-amino-imidazole. These structures were disclosed as having cardiovascular and anti-inflammatory activities.

In addition, several drugs are known which substitute a methylene group for the bridging amino group in the imidazoline series, compounds such as oxymetazoline, naphazoline and tolazoline are examples. The Ruffolo review indicates at page 95 that "replacement of the nitrogen bridge of clonidine with a methylene bridge has little effect on $\alpha_2$ adrenoceptor activity . . . " and elsewhere on p. 95 that the "replacement of the nitrogen atom in clonidine-like imidazolines with either carbon or sulfur produces only a small reduction in $\alpha_2$ adrenoceptor activity".

The background of the division of adrenergic receptor system into differing categories and subtypes can be briefly described as follows. Historically, adrenoceptors were first divided in $\alpha$ and $\beta$ types by Ahlquist in 1948. This division was based on pharmacological characteristics. Later, $\beta$-adrenoceptors were subdivided into $\beta_1$ and $\beta_2$ subtypes, again based on a pharmacological definition by comparison of the relative potencies of 12 agonists. The $\alpha$-adrenoceptors were also subdivided into $\alpha_1$ and $\alpha_2$ subtypes, initially based on a presumed localization of $\alpha_1$ receptors postsynaptically and $\alpha_2$ presynaptically. Now, however, this physiologic division is no longer used and it is generally accepted that the most useful way to subdivide the $\alpha$-adrenoceptors is based on pharmacology using affinities for the antagonists yohimbine and prazosin. At $\alpha_1$ receptors, prazosin is more potent that yohimbine, whereas the $\alpha_2$ receptors, yohimbine is more potent than prazosin. Bylund, et al. first suggested in 1981 that there possibly existed subtypes of the $\alpha_2$-adrenoceptors on the basis of radioligand binding studies. This initial work was done with various tissues taken from various species. While receptor heterogeneity among species is considered to be important, the term 'subtype' is usually reserved by pharmacologists for heterogeneity which can be demonstrated within the same species and ideally within a single tissue. Bylund and coworkers have later demonstrated that some regions of the human and rat brain contain two populations of $\alpha_2$-adrenoceptors sites which differ in their affinity for prazosin by 30- to 40-fold.

This finding supports the division of the $\alpha_2$ receptor into A and B subtypes. More recently there have been reports of a third alpha subtype receptor called 2C.

Some examples of alpha$_2$ ($\alpha_2$) adrenergic receptor agonists well known in the art are:

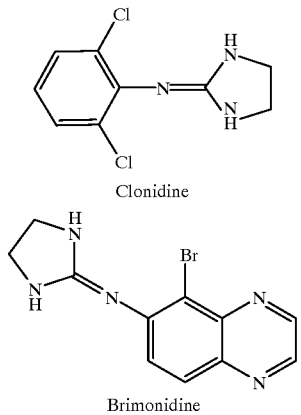

Clonidine

Brimonidine

Clonidine is clinically useful as a hypotensive agent, and has been studied as a nasal decongestant and as an ocular hypotensive agent and as an anesthetic adjunct. The mechanism of action of clonidine has been described as a centrally acting $\alpha_2$ adrenergic partial agonist, however, clonidine also has hypotensive cardiovascular effects. It was reported that clonidine binds to both $\alpha_2$ and imidazoline receptors and that the binding to the imidazoline receptors mediates the blood pressure lowering side effects of clonidine. [See e.g. Codd, E. E., et al. Life Sci., 56 (2) p. 63–74 (Dec. 2, 1994) and Ernsberger, P., et al., Cardiovasc. Drugs Ther., 8 (Suppl. 1) pp. 27–41 (March 1994)] Brimonodine (UK 14,304) is a newer $\alpha_2$ adrenergic agent which possesses superior therapeutic action as an ocular hypotensive, and has been tested in other $\alpha$2 agonist responsive conditions. Brimonidine, as is shown by the data in table I at Example 4 also shows significant imidazoline receptor binding affinity. Other activities inferred by I-receptor studies are stimulation of insulin release from pancreatic $\beta$-cells via coupling to ATP-sensitive K+ channels and inhibition of sodium reabsorption in the tubules of the kidneys. It has now been suggested by the present inventors that the imidazoline receptor is a nonfunctional binding site. [See Munk, S. A., et al, *J. Med. Chem.* 39 (6) 1193–1195(1996).]

A few compounds which have been reported to be a2A selective are dexmedetomidine and oxymetazoline.

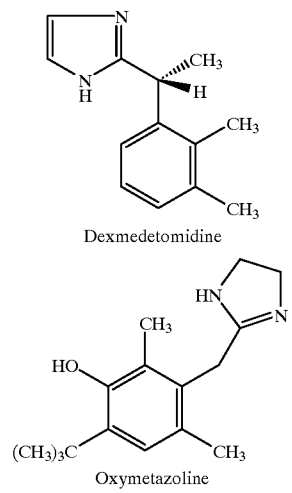

Dexmedetomidine

Oxymetazoline

The identification of subtypes of the $\alpha_2$ receptor has progressed faster than complete pharmacological and physiological characterization of them. Nevertheless, $\alpha_{2A}$ receptors have been identified in the ciliary body of the eye, and so are postulated to have a controlling mechanism in ocular hypertension and symptomatology of glaucoma (see Sin, Y. et al., *J. Ocul. Pharmacol.* 10(1) pp. 359–69 (1994). Alpha $_{2A}$ receptors have also been studied in pain perception, or alternatively, pain alleviation (see Millan, M. J., *Eur. J. Pharmacol.*, 215(2–3) pp. 355–6 (1992).

A selective or subtype selective agonist as the term is used in this invention indicates a compound that binds to, and activates, a specific receptor subtype in preference to other receptors of related but different subtype(s). For example, a compound that binds to and activates the $\alpha_{2A}$ subtype receptor in preference to the $\alpha_{2B}$ or $\alpha_{2C}$ subtype receptors is an $\alpha_{2A}$ selective agonist. Activation means that the receptor is induced to initiate a biochemical event that is controlled or operated by that particular receptor. Activation can further be thought of in terms of a signal transduction process which mediates the signal triggered by receptor activation to intracellular effector structures.

From this summary of the state of the art it is apparent that compounds which are selective $\alpha_2$ agonists possess valuable therapeutic utility for treating glaucoma and pain, and for producing sedation.

SUMMARY OF THE INVENTION

This invention covers methods of using compounds of formula I selective agonism of $\alpha_2$ adrenoceptors Formula I

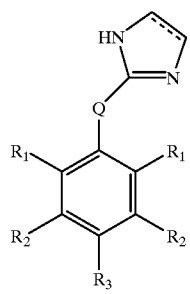

wherein Q is NH or CH$_2$, a broken line parallel to and adjacent a solid line indicates a single or a double bond, each R$_1$ is independently H, alkyl of 1 to 4 carbon atoms or a halogen atom, each R$_2$ is independently H or an atom or functional group chosen from the group consisting of —N(R$_4$)$_3$, —OR$_4$, F, Cl, Br and —SR$_4$, and wherein each R$_4$ is independently chosen from the group consisting of hydrogen, alkyl of 1 to 4 carbon atoms and alkylcarbonyl of 1 to 5 carbon atoms, and R$_3$ is independently chosen from the group of values for R$_1$ and R$_2$, or R$_2$ and R$_3$ together can form a 5 or 6 membered ring, which can optionally bear methyl, ethyl or oxo substituents, fused to the aryl ring, provided that in either case at least one R$_2$ is —N(R$_4$)$_3$, —OR$_4$, F, Cl, Br, or —SR, and that the heteroatom bonds directly to the aryl ring.

Preferably the present invention provides a method of treating elevated intraocular pressure, nasal congestion or diarrhea in a mammal comprising administering to said mammal a therapeutically effective amount of a compound of the formula II

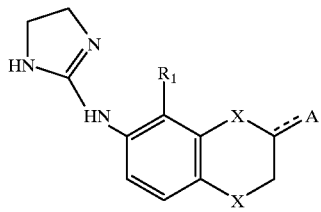

wherein R$_1$ is H, alkyl of 1 to 4 carbon atoms or a halogen atom, X is O or NH and A is H or an oxo group and wherein said compound does not cause a concomitant reduction in blood pressure of said mammal.

More preferably in the method of the present invention the compound of formula II has the structure

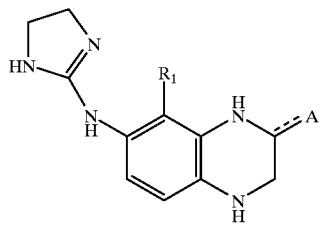

wherein R$_1$ represents methyl or bromine and A is hydrogen or an oxo group.

Most preferably in the method of the present invention the compound of formula II has the structure

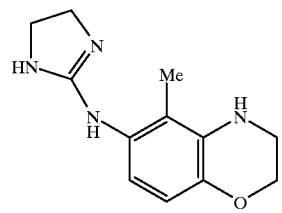

Pharmaceutically acceptable salts of the compounds of formula I are also within the scope of the present invention. Pharmaceutically acceptable acid addition salts of the compounds of the invention are those formed from acids which form non-toxic addition salts containing pharmaceutically acceptable anions, such as the hydrochloride, hydrobromide, hydroiodide, sulfate, bisulfate, phosphate or acid phosphate, acetate, maleate, fumarate, oxalate, lactate, tartrate, citrate, gluconate, saccharate, or p-toluenesulfonate salts. A pharmaceutically acceptable salt may be any salt which retains the activity of the parent compound and does not impart any deleterious or untoward effect on the subject to which it is administered and in the context in which it is administered.

Organic amine salts may be made with amines, particularly ammonium salts such as mono-, di- and trialkyl amines or ethanol amines. Salts may also be formed with caffeine, tromethamine, and similar molecules. Where there is a nitrogen sufficiently basic as to be capable of forming acid addition salts such may be formed with any inorganic car organic acids or alkylating agent such as methyl iodide. Any of a number of simple organic acids such as mono-, di-, or tri-acid may also be used. A pharmaceutically acceptable salt may be prepared for any compound of the invention having a functionality capable of forming such a salt, e.g., an acid salt of an amine group.

General Embodiments

Definitions

The terms "ester" and "amide" as used here refer to and cover any compound falling within the definition of those terms as classically used in organic chemistry.

Some compounds of the present invention contain the (2-imidazolyl) amino structure which is represented as:

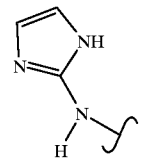

This group attaches via the exocyclic nitrogen to the aryl ring. Other compounds or the present invention have the (2-imidazolinyl) amino group represented in structure by:

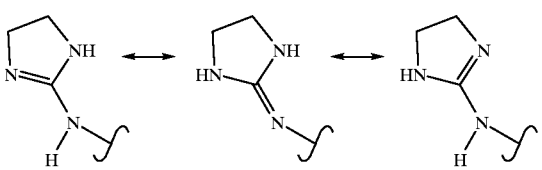

These compounds exist as tautomers (formally equivalent isomers capable of interchanging double bond positions and a proton between the heteroatoms) wherein the double bond can shift from one nitrogen to another either within or without the ring but always terminating at the 2-carbon of the ring. The chemical nomenclature of these compounds is: 2-amino-imidazolines for the forms where the double bond is positioned within the ring and 2-imino-imidazolidines when the double bond is positioned outside the ring. No tautomeric form of these compounds places a double bond at the 4–5 position of the imidazole ring.

A further group of the present invention involves compounds which have in imidazoline ring but not an exocyclic amino group, but rather a methylene group in its place. Compounds of this type can tautomerize to give different double bond position within the ring only as shown below.

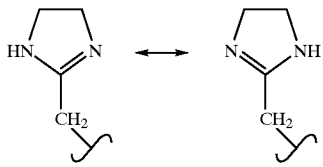

Hydrogen-bond acceptors are well-defined in the art [see for example, Wilson and Gisvold's Textbook of Organic Medicinal and Pharmaceutical Chemistry., R. F. Doerge (ed.) J. B. Lipincott Co. 1982 HP 41–43 or Physical Organic Chemistry, N. S. Isaacs Universities Press (Belfast) Ltd., 1987 pp. 62–67]. A hydrogen bond is a bond in which a hydrogen atom serves to hold two other atoms together. These "other atoms" must themselves be capable of forming hydrogen bonds. Atoms with hydrogen bond forming capability have at least one unshared electron pair together with a complete octet of electrons. A list of atoms contemplated by the invention includes: F, O, N, Cl, Br and S. The H-bond consists of an attractive force which exists between a hydrogen atom covalently bound to an atom from the list given above (e.g. a hydroxy group, —O—H) and a second atom, not necessarily the same, from the list. The lone pair atom which has the covalent bond to hydrogen is; called the hydrogen bond donor. The other atom which hydrogen bonds with this donated hydrogen is called the hydrogen bond acceptor.

Some groups such as hydroxy or primary or secondary amine can act as both hydrogen bond donors and hydrogen bond acceptors. Groups such as ethers or tertiary amines are hydrogen bond acceptors only. The valence of quaternary amines which have no free lone pair are incapable of being hydrogen bond acceptors. Hydrogen bond acceptor groups specifically contemplated by the present invention are primary, secondary, and tertiary amines, hydroxyl and ethers functions, amides and esters, fluoro, chloro and bromo groups and thiols and thioethers.

The term "alkyl" as used here refers to and includes normal and branch chained alkyl groups. The term "lower alkyl", unless specifically stated otherwise, includes normal alkyl of 1 to 4 carbons, branch chained alkyl of 3 or 4 carbons. Similarly, the terms "alkenyl" and "alkynyl" include normal and branch chained groups having 2 to 4 carbons when the chains are normal, and 3 or 4 carbons when the chains are branched.

BRIEF DESCRIPTION OF THE DRAWING FIGURES

FIG. I compares the effect of clonidine and a representative compound of this invention for lowering intraocular pressure (IOP).

FIG. II compares the effect of clonidine and a representative compound of this invention for lowering blood pressure.

DETAILED DESCRIPTION OF THE INVENTION

Figure 1A:
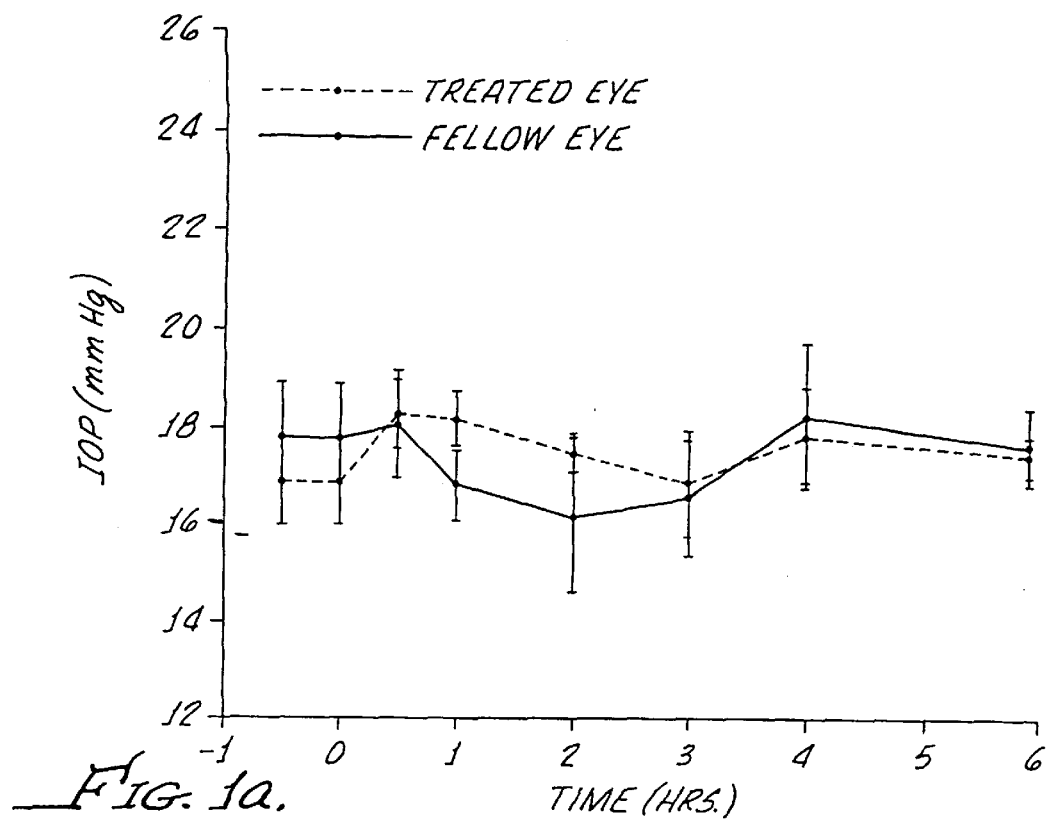

The compounds of Formula I as described above including all stereoisomers, tautomers as previously defined and mixtures thereof which comply with the constraints of the present compounds are included within the scope of the present invention.

The present compounds may be prepared in a manner analogous to the procedures in: Commonly assigned PCT application 95/US/01150 filed on Jan. 25, 1995 by Munk, et al. discloses certain phenyl-2-amino-imidazoles which have subtype selected $\alpha_{2A}$ activity and methods for making them. The contents of this PCT application are hereby incorporated by reference in their entirety. U.S. Pat. No. 5,091,528 by Gluchowski and commonly assigned with the present application discloses methods of making (2-amino-imidazolinyl)-benzoxazine compounds encompassed by the methods of the present invention. The content of U.S. Pat. No. 5,091,528 is hereby incorporated by reference in its entirety. Similarly, U.S. Pat. No. 5,112,322 by Gluchowski and also commonly assigned discloses methods of making (2-amino-imidazolinyl)-tetrahydroquinoxaline compounds and is hereby incorporated by reference in its entirety. Other compounds, such as oxymetazoline, are well-known compounds in the art and are commercially available.

The present meta-substituted aryl linked imidazolines and imidazoles are useful to provide one or more desired therapeutic effects in a mammal. Among the desired therapeutic effects are an alteration, preferably a decrease in the rate of fluid transport in the gastrointestinal tract of a mammal, a reduction in or maintenance of the intraocular pressure in at least one eye of a mammal; and an increase in the renal fluid flow in at least one kidney of a mammal, or a decrease in nasal. congestion in the air passages of a mammal. Thus, for example, the present compounds may be used as a antidiarrhea agent, a medication for use in the treatment or management of glaucoma, a medication for use in the treatment or management of kidney disease and/or a treatment for congested nasal passages. One important feature of many of the present compounds is that the desired therapeutic effect is achieved with reduced or absent side effects, in particular, lacking effects on the blood pressure or the mammal to which the present compound or compounds is/are administered.

Preferred compounds of the invention with reference to the Examples 1–24 in Table 1 are those compounds which show high affinity for $\alpha_2$ receptors (low Ki values) in the binding assays. Particularly preferred are those compounds in which the Ki (binding affinity) value for the $\alpha_2$ receptors is from 0.0001 to 10. With respect to the structural features which are preferred in the present invention, the elements which are preferred in providing the desired binding respect to the structural features which are preferred in the present invention, the elements which are preferred in providing the desired binding characteristics are the presence of a fused ring at $R_2$ and $R_3$, more preferably with a nitrogen atom bonding to the aryl ring at $R_2$ and even more preferably with a nitrogen atom bonding to the aryl ring at $R_2$, and even more preferably with a nitrogen or oxygen atom bonding to the aryl ring at $R_3$. Other preferred embodiments include compounds of formula 1 wherein both $R_1$s are methyl, one $R_2$ is hydroxy or methoxy, the other $R_2$ is hydrogen, and $R_3$ is -butyl.

Any suitable method of administering the present compound or compounds to the mammal to be treated may be used. The particular method of administration chosen is preferably one which allows the present compound or compounds to have the desired therapeutic effect in an effective manner, e.g., low medication concentration and low incidence of side effects. In many applications, the present compound or compounds are administered to a mammal in a manner substantially similar to that used to administer $\alpha_2$ agonists, to obtain the same or similar therapeutic effect.

The invention is further illustrated by the following non-limiting examples which are illustrative of specific modes of practicing the invention and are not intended as limiting the scope of the appended claims.

TABLE 1
| Structure | Kı | | | | | | |
|---|---|---|---|---|---|---|---|
| | α1 | α_{2A} | α_{2B} | α_{2C} | I_1 | I_{2A} | I_{2B} |
| Example 1 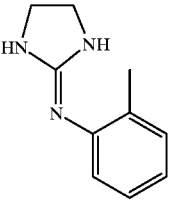 | 5,034 | 8.9 | 49 | 70 | 12 | 1,200 | |
| Example 2 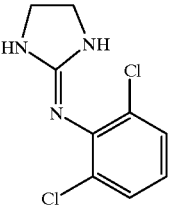 | 513 | 3.8 | 8.3 | 30 | 8.9 | 10,000 | 12,452 |
| Example 3 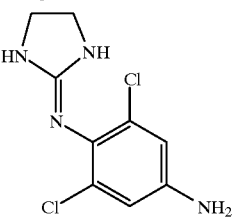 | 181 | 2.9 | 4.8 | 21 | 19 | 64,790 | 38,642 |
| Example 4 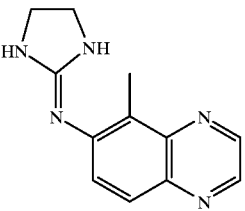 | 1,433 | 2 | 17 | 27 | 48 | 5,199 | 155 |
| Example 5 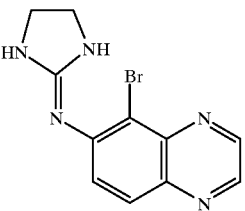 | 1,850 | 2.7 | 52 | 44 | 17 | 7,193 | 614 |
| Example 6 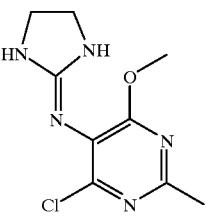 | 38,573 | 147 | 1,029 | 2,012 | 56 | 100,000 | 100,000 |

TABLE 1-continued

| Structure | $K_i$ | | | | | | |
|---|---|---|---|---|---|---|---|
| | α1 | α$_{2A}$ | α$_{2B}$ | α$_{2C}$ | I$_1$ | I$_{2A}$ | I$_{2B}$ |
| Example 7 | 5,100 | 35 | 262 | 463 | 1,988 | 100,000 | 10,000 |
| Example 8 | 8,715 | 9.6 | 139 | 124 | 100,000 | 100,000 | 10,000 |
| Example 9 | 1,117 | 6.1 | 47 | 120 | 4,575 | 7,561 | 4,588 |
| Example 10 | 6,606 | 24 | 194 | 293 | 3,952 | 24,827 | 3,256 |
| Example 11 | 2,403 | 3.1 | 28 | 20 | 1,835 | 1,084 | 2,032 |

TABLE 1-continued
| Structure | α1 | α$_{2A}$ | α$_{2B}$ | α$_{2C}$ | I$_1$ | I$_{2A}$ | I$_{2B}$ |
|---|---|---|---|---|---|---|---|
| Example 12 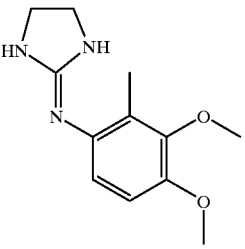 | 1,452 | 5.2 | 196 | 93 | 340 | 100,000 | 507 |
| Example 13  | 129 | 0.25 | 4 | 3.5 | 831 | 100,000 | 1,223 |
| Example 14 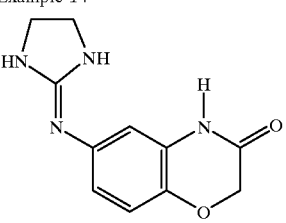 | 8.987 | 52 | 842 | | 11,600 | 4,500 | 6,517 |
| Example 15 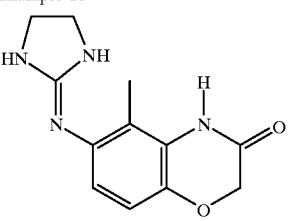 | 2,262 | 17 | 241 | 134 | 100,000 | | |
| Example 16 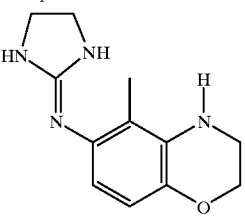 | 473 | 1.2 | 30 | 8.9 | 7,112 | 100,000 | 12,135 |
| Example 17 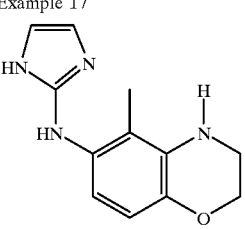 | 14,784 | 6.3 | 436 | 229 | 5,300 | 27,035 | 9,283 |

TABLE 1-continued
| Structure | Ki | | | | | | |
|---|---|---|---|---|---|---|---|
| | α1 | α$_{2A}$ | α$_{2B}$ | α$_{2C}$ | I$_1$ | I$_{2A}$ | I$_{2B}$ |
| Example 18 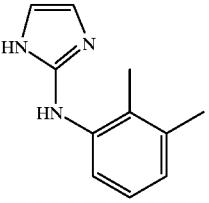 | 5,214 | 52 | 295 | 180 | 19 | 141 | 13 |
| Example 19 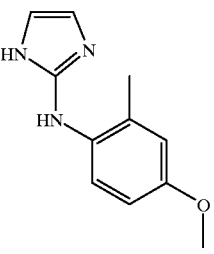 | 7,613 | 10 | 434 | 512 | 13 | 6,180 | 179 |
| Example 20 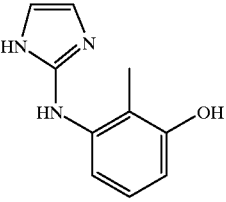 | 11,316 | 30 | 895 | 457 | 412 | | |
| Example 21 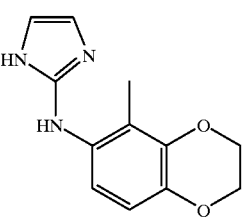 | 2,147 | 1.7 | 82 | 19 | 444 | 7,708 | 686 |
| Example 22 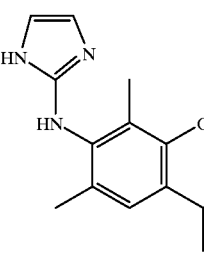 | 4.175 | 4.9 | 221 | 88 | 4,320 | 100,000 | 870 |

TABLE 1-continued

| Structure | α1 | $\alpha_{2A}$ | $\alpha_{2B}$ | $\alpha_{2C}$ | $I_1$ | $I_{2A}$ | $I_{2B}$ |
|---|---|---|---|---|---|---|---|
| Example 23 | 199 | 0.27 | 97 | 13 | 7,417 | 12,873 | 2,692 |
| Example 24 | 30,550 | 31 | 1,156 | 212 | 227 | 6,367 | 36 |

Experimental Assays: Binding Affinities and Receptor Activation

Receptor Binding Assays

EXAMPLE 25

Tissue preparation: Membrane suspensions were prepared from human cerebral cortex (HDD, for α1 receptors) obtained from the UCI Organ and Tissue Bank. Briefly, tissues (1 g) were homogenized in 25 mL of ice-cold 5 mM Tris, pH 7.4 with a Polytron homogenizer for 30 sec at setting #7, and centrifuged for 10–12 minutes at 300× g at 4° C. The supernatant was filtered through 2 layers of gauze and diluted 1:2 with 50 mM Tris-HCl buffer, pH 7.4, then centrifuged at 49,000× g for 20 minutes. The pellet fraction was washed 3 times (resuspended in Tris-HCl buffer and centrifuged for 20 minutes; at 49,000× g). The pellet was then stored at −80° C. until the binding assay.

Cell preparation: Chinese hamster ovary (CHO) cells expressing the human $\alpha_{2A}$ and human $\alpha_{2C}$ (CHO-C10 and CHO-C4 respectively) receptors and CHO cells (CHO-RNG) expressing the rat $\alpha_{2B}$, adrenoceptor were grown to near confluence in Dulbecco's modified Eagle's medium supplemented with 10% fetal bovine serum using standard cell culture methods. Cells were harvested by scraping and placed into cold buffer of the following composition: 50 mM Tris-HCl, 5 mM EDTA, pH 7.4). Cells were then homogenized with a Polytron homogenizer for 2×10 sec at setting #7, and centrifuged for 20 minutes at 49,000× g. The pellet fraction was washed (resuspended in Tris-HCl, pH 8 buffer and centrifuged for 15–20 minutes at 49,000× g) 2 times and stored at −100° until binding assay.

Binding Studies: The radioligands [$^3$H]rauwolscine (specific activity 80 Ci/mmol) and [$^3$H]prazosin (specific activity 76 Ci/mmol) were obtained from New England Nuclear, Boston, Mass. Frozen membrane pellet was resuspended in 25 mM glycine/glycine, pH 7.5 and incubated with radioligand under the following conditions: CHO-C10, CHO-RNG, CHO-C4-[$^3$H]rauwolscine, 22° C., 30 minutes; RKC-[$^3$H]rauwolscine, 0° C., 120 minutes; and, HCC-[$^3$H] prazosin, 22° C., 30 minutes in a final volume of 500 ul. At the end of the incubation period, the samples were filtered through glass filters (Whatman GF/B) in a 96 well cell harvester and rapidly washed four times with 4 mL of iced-cold 50 mM Tris-HCl buffer. The filters were then oven dried and transferred to scintillation vials containing 10 mL of Beckman's Ready Protein® scintillation cocktail for counting. Specific binding defined by 10 uM phentolamine for in competition studies were as follows: 2.4 nM [$^3$H] brimonidine-RbICB 62%; 2.4 nM [$^3$H]rauwolscine-RbICB 75%; 2 nM [$^3$H]rauwolscine-RbKc 88%; 0.3 nM [$^3$H] rauwolscine-CHO-C10 99%; 0.4 nM [$^3$H]rauwolscine-CHO-RNG 99%, 0.3 NM [$^3$H]prazosin 87%; and 1 nM [$^3$H]rauwolscine-CHO-C4 90%. Protein concentrations were determined with a protein assay kit from Bio Rad. Binding isotherms, equilibrium dissociation and affinity constants were analyzed and determined by the non-linear least squares curve fitting programs EBDA (BioSoft) or AccuFit Competition/Saturation by Beckman.

EXAMPLE 26

Cell Preparation: Chinese hamster ovary (CHO) cells expressing the human $\alpha_{2A}$ (CHO-C10) and the rate $\alpha_{2B}$ (CHO-RNG) human $\alpha_{2A}$ adrenoceptors were grown to near confluence in Dulbecco's modified Eagle's medium supplemented with 10% fetal bovine serum using standard cell culture methods. Cells were harvested by scraping and placed into cold buffer of the following composition: 50 mM Tris-HCl, 5 mM EDTA, pH 7.4). Cells were then homogenized with a Polytyron homogenizer for 2×10 sec at setting #7, and centrifuged for 20 minutes at 49,000× g. The pellet fraction was washed (resuspended in Tris-HCl, pH 8 buffer and centrifuged for 15–20 minutes at 49,000× g) 2 times and stored at 100° C. until binding assay.

Binding studies: Determination of Ki

The radioligands [$^3$H] rauwolscine (specific activity 80 Ci/mmol) and [$^3$H] prazosin (specific activity 76 Ci/mmol) were obtained from New England Nuclear, Boston, Mass. Frozen membrane pellet was resuspended in 25 mM glycine/ glycine, pH 7.4 and incubated with radioligand under the following conditions: CHO-C10, CHO-RNG, CHO-C4-[$^3$H]rauwolscine, 22° C., 30 min.; and, HCC-[$^3$H]prazowsin, 22° C., 30 minutes in a final volume of 500 ul. At the end of the incubation period, the samples were filtered through glass fiber filters (Whatman GF/B) in a 96 well cell harvester and rapidly washed four times which 4 mL of iced-cold 50 mM Tris-CHI buffer. The filters were then oven dried and transferred to scintillation vials containing 5 mL of Beckman's Ready Protein® scintillation cocktail for counting. Specific binding defined by 10 uM phentolamine for competition studies were as follows: 0.3 nM[$^3$H]rauwolscine-CHO-C10 99%; 0.4 nM[$^3$H]rauwolscine-CHO-RNG 99%, and 0.3 nM [$^3$H]prazosin-HCC 87%. Protein concentrations were determined with a protein assay kit from Bio lad. Binding isotherms, equilibrium dissociation and affinity constants were analyzed and determined by the non-linear least squares curve fitting programs AccuFit Competition/Saturation by Beckman.

Preparation of Bovine ventrolateral medulla (BVLM) membranes

EXAMPLE 27

Fresh bovine brain stems were obtained from a local slaughter house. After removal of pia-arachnoid, the medulla was isolated by dissecting the brain stem about 1 cm posterior and 1 cm caudal to the obex. The ventral quadrants of the medulla excluding the pyramids were used as the VLM. For each preparation, 30 to 40 VLM were used. Initial homogenization was performed in 20 volumes of 5 mM HEPES buffer (pH 7.4 at 4° C.) containing 250 mM sucrose, 50 uM Calpain I inhibitor (Boehginer Mannheim, Indianapolis, Ind.), 100 uM 1,10-phenanthroline (Sigma, St. Louis, Mo.) and 50 uM Pefabloc (Boehginer Mannheim, Indianapolis, Ind.), using Virtis homogenizer at setting 7 with three 10 second pulses, followed by three passes in a teflon-glass tissue homogenizer. The inhibitors were added to prevent degradation by proteases and peptidases. The homogenates were then centrifuged at 1000× g for 10 min and the resulting pellets were re-homogenized and centrifuged. Supernatants resulted from both runs were combined and centrifuged for 20 min at 48000× g. The pellets obtained were resuspended in a teflon-glass homogenizer in 50 mM Tris-HCl with 5 mM EDTA (pH 7.7 at 4° C.), centrifuged, and resuspended in 50 mM Tris-HCl with 25 mM NaCl, pH 7.7 at room temp. To remove endogenous ligands, the homogenate was incubated 30 min at room temp before it was centrifuged for 20 min at 48000× g. The pellets were then washed with 50 mM Tris-HCl buffer, (pH 7.4 at 4° C.) and loaded on top of 5 mM HEPES/0.85 M sucrose (pH 7.4 at 4° C.). Pellets obtained after centrifugation at 48000× g for 20 min were saved. The fatty connective tissue on the top layer was discarded. The partially purified VLM membrane pellets were then washed twice with 50 mM Tris-HCl, pH 7.7 at 4° C., flash frozen in dry ice/acetone slush, and stored at −100° C. until use. Receptor binding experiments were performed within days after the membrane preparation.

$I_1$ imidazoline receptor binding assay

EXAMPLE 28

$I_1$ imidazoline receptor binding affinity was determined from radioligand binding of $^3$H-clonidine (NEN, Boston, Mass.) to bovine VLM membranes. Specific activity of $^3$H-clonidine was 43 Ci/mmol. Kd of $^3$H-clonidine binding to the $I_1$ imidazoline receptor was determined by saturation experiments and Ki of other ligands studied were determined by competition experiments. The radioligand binding assay was performed in Teflon 96-wells with the Biomek-1000 robotics (Beckman Instruments, Fullerton, Calif.). Each well contained 4 mN $^3$H-Clonidine and 0.3 to 0.5 mg of bovine VLM protein in 5 mM HEPES buffer containing 0.5 mM EGTA and 0.5 mM $MgCl_2$, pH 7.4 (0.1 mM ascorbic acid was added just before the protein). After 50 min of incubation at 25° C., the reaction was terminated by rapid filtration over Whatman GF/B filters treated with 0.1% polyethyleneimine and washed with 12 ml ice cold 50 mM Tris-HCl, pH 7.4 at 4° C. in a Brandel Harvester (Brandel, Gaithersburg, Md.). Both 'hot' and 'cold' saturation experiments were performed. In 'hot' saturation experiments, studies were performed with $^3$H-clonidine ranging from 0.1 to 50 nM. In 'cold' saturation experiments, studies were performed with 2 nM $^3$H-clonidine with 20 different concentrations of the unlabeled clonidine, ranging from 0.1 nM to 1 uM unlabeled clonidine. Non specific binding was defined by parallel incubations containing $10^{-5}$ M phentolamine or naphazoline. Imidazoline binding was determined by parallel incubations in which the alpha-adrenergic sites were masked with $10^{-5}$ M norepinephrine. During competition experiments, ligands of 20 concentrations ranged from $10^{-11}$ to $10^{-4}$ were used. Radioactivity was counted in a Beckman LS-3801 scintillation counter. Data were captured and analyzed with Accufit saturation and competition softwares modeled both for one-site and two-site fits (Beckman Instruments, Fullerton, Calif.) using an IBM compatible computer. All experiments were repeated at least twice.

Representative compounds of the present invention were tested according to the procedures given above. Results of these tests are tabulated in Table 1 above as specific examples. The receptor binding studies and $K_1$ are measures of the affinity of a compound for a particular receptor.

EXAMPLE 29

Figure 1B:
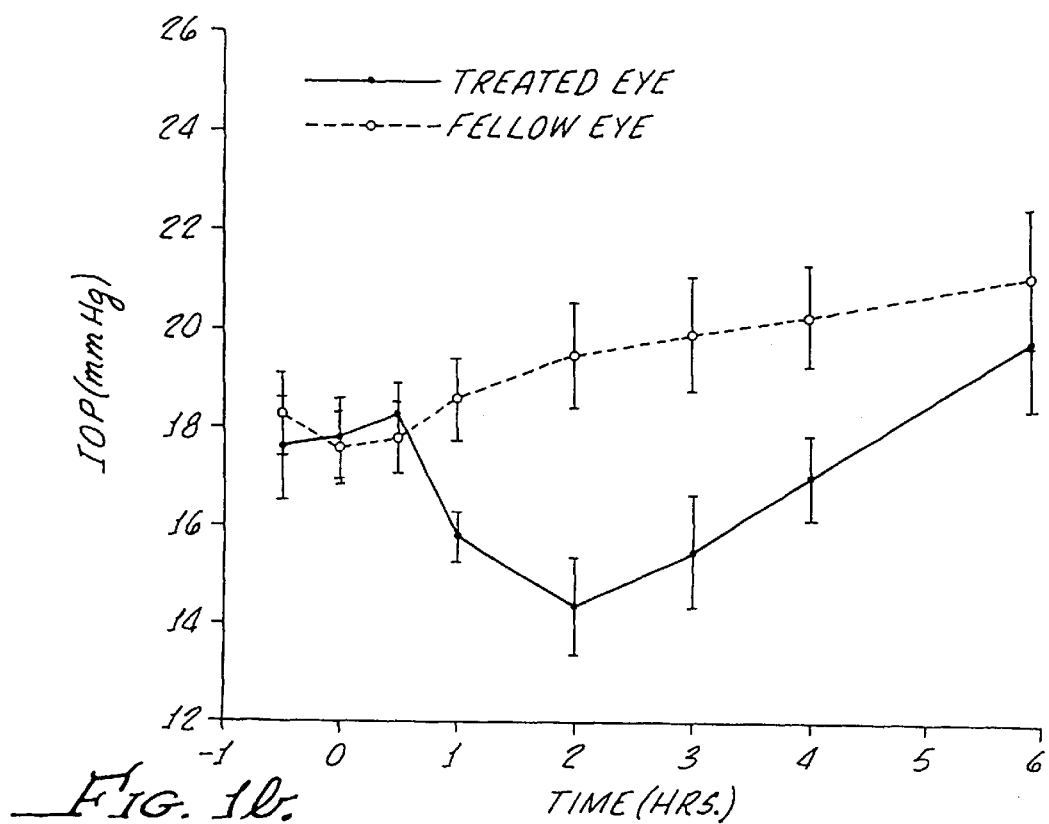

The compound of Example 16 was compared to clonidine for lowering intraocular pressure (IOP) by topical administration of a single drop of 0.001% of the compound in an ophthalmically acceptable vehicle to one eye of a rabbit. The untreated eye was used as the control. The results are reported in FIG. 1. As shown, clonidine shows a systemic effect, in that the IOP of the untreated eye is lowered to the same extent as the treated eye. In contrast, the eye treated with the compound of Example 16 showed a greater effect in lowering IOP than clonidine without lowering IOP in the untreated eye.

EXAMPLE 30

Figure 2:
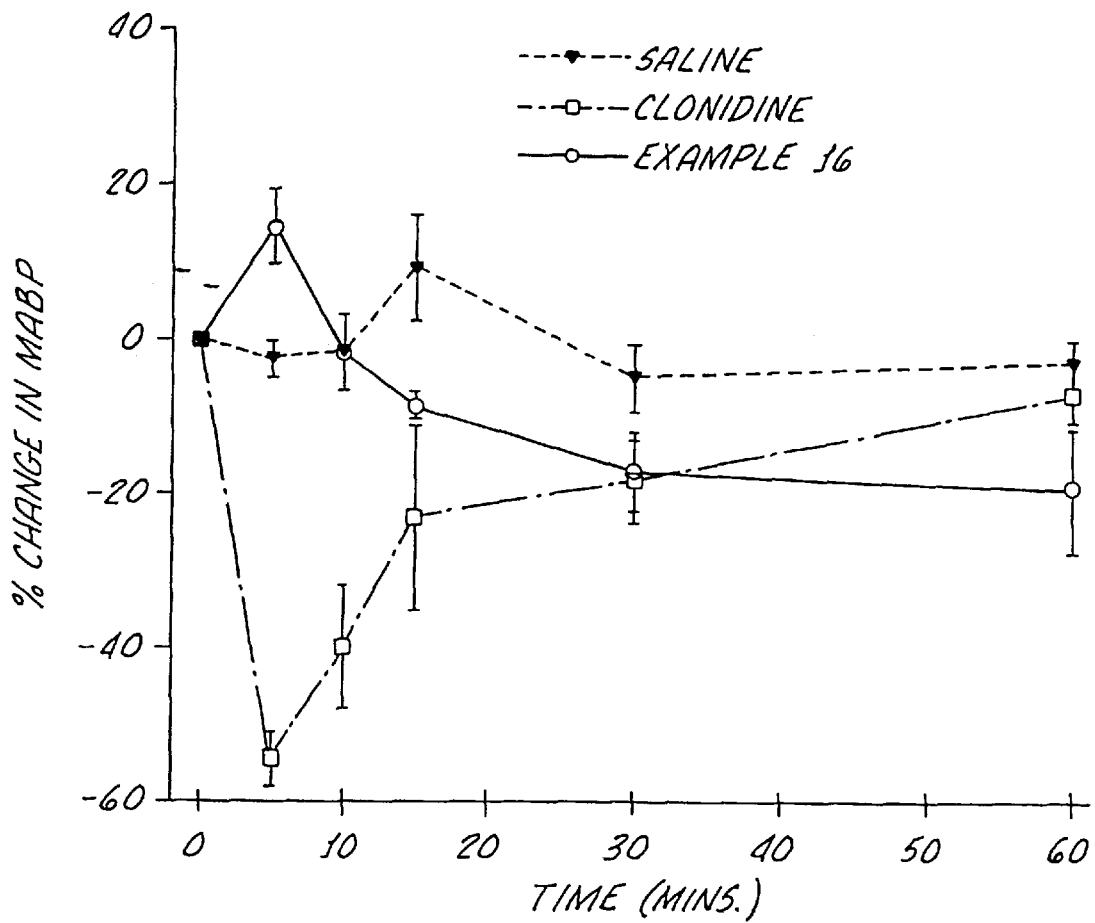

The compound of Example 16 and clonidine were tested for systemic effect by injecting 10 ug/kg of each compound into a rabbit. In comparison to a saline control, the clonidine lowered the mean arterial blood pressure, substantially, while the compound of Example 16 did not effectively lower the mean arterial blood pressure. These results are reported in FIG. 2.

While the invention has been described in terms of certain preferred embodiments and specific examples, they are not intended as limiting the scope of the present invention which should be determined solely on the basis of the appended claims, as such claims are read in light of the disclosure.

We claim:

1. A method of treating elevated intraocular pressure in a mammal comprising administering to said mammal a therapeutically effective amount of a compound of the formula II

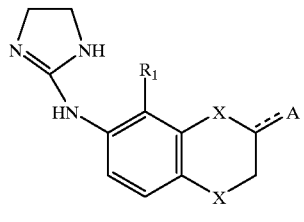

wherein R1 is H or alkyl of 1 to 4 carbon atoms, one X is NH and the other X is O or NH and A is H or an oxo group and wherein said compound does not cause a concomitant reduction in blood pressure of said mammal.

2. The method of claim 1 wherein the compound of formula II has the structure

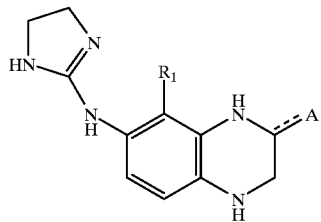

wherein $R_1$ represents methyl or bromine and A is hydrogen or an oxo group.

3. A method of treating nasal congestion in a mammal comprising administering to said mammal a therapeutically effective amount of a compound of the formula II

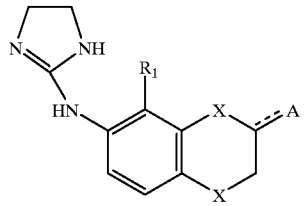

wherein R1 is H or alkyl of 1 to 4 carbon atoms, one X is NH and the other X is O or NH and A is H or an oxo group and wherein said compound does not cause a concomitant reduction in blood pressure of said mammal.

4. The method of claim 3 wherein the compound of formula II has the structure

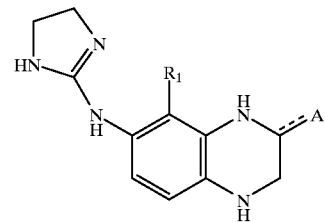

wherein $R_1$ represents methyl or bromine and A is hydrogen or an oxo group.

5. The method of claim 3 wherein the compound of formula II has the structure

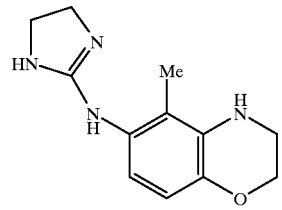

6. A method of treating diarrhea in a mammal comprising administering to said mammal a therapeutically effective amount of a compound of the formula II

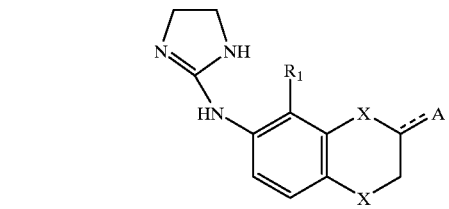

wherein R1 is H or alkyl of 1 to 4 carbon atoms, one X is NH and the other X is O or NH and A is H or an oxo group and wherein said compound does not cause a concomitant reduction in blood pressure of said mammal.

7. The method of claim 6 wherein the compound of formula II has the structure

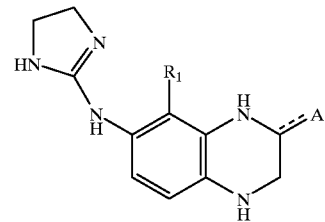

wherein $R_1$ represents methyl or bromine and A is hydrogen or an oxo group.

* * * * *

UNITED STATES PATENT AND TRADEMARK OFFICE
CERTIFICATE OF CORRECTION

PATENT NO.  : 6,087,361
DATED       : July 11, 2000
INVENTOR(S) : Munk et al

It is certified that error appears in the above-indentified patent and that said Letters Patent is hereby corrected as shown below:

In the abstract, line 1 after the formula, delete "or" and insert in place thereof --of--
Column 7, line 3; delete "$n^2$-amino" and insert in place thereof --2-amino--
Column 7, line 24; delete "HP" and insert in place thereof --pp.--
Column 7, line 35; delete "is;" and insert in place thereof --is--
Column 8, line 15; delete "5,112,322" and insert in place thereof --5,112,822--
Column 8, line 27; delete "nasal." and insert in place thereof --nasal--
Column 8, line 54; delete "-butyl" and insert in place thereof --t-butyl--
Column 18, line 37; delete "in"
Column 19, line 7; delete "CHI" and insert in place thereof --CH1--

Signed and Sealed this

Tenth Day of April, 2001

*Attest:*

NICHOLAS P. GODICI

*Attesting Officer*    Acting Director of the United States Patent and Trademark Office